United States Patent
Levin et al.

(10) Patent No.: US 6,169,216 B1
(45) Date of Patent: Jan. 2, 2001

(54) PRODUCTION OF PHENOL

(75) Inventors: Doron Levin, Bala Cynwyd; Jose G. Santiesteban; James C. Vartuli, both of West Chester, all of PA (US)

(73) Assignee: Mobil Oil Corporation, Fairfax, VA (US)

( * ) Notice: Under 35 U.S.C. 154(b), the term of this patent shall be extended for 0 days.

(21) Appl. No.: 09/296,852

(22) Filed: Apr. 22, 1999

(51) Int. Cl.$^7$ ..................................................... C07C 37/08
(52) U.S. Cl. ........................ 568/798; 568/385; 568/485; 568/741; 568/754; 568/768
(58) Field of Search ..................... 568/798, 385, 568/768, 741, 754, 485

(56) References Cited

U.S. PATENT DOCUMENTS

| 4,490,565 | 12/1984 | Chang et al. | 568/798 |
| 4,490,566 | 12/1984 | Chang et al. | 568/798 |
| 4,898,995 | 2/1990 | Knifton et al. | 568/798 |

OTHER PUBLICATIONS

M. Hino et al., *Journal of the American Chemical Society*, Oct. 10, 1979, pp. 6439–6441.

*Primary Examiner*—Sreeni Padmanabhan

(57) ABSTRACT

A process for producing phenol and acetone from cumene hydroperoxide is described in which the cumene hydroperoxide is contacted with a solid-acid catalyst comprising a sulfated transition metal oxide, preferably sulfated zirconia.

9 Claims, No Drawings

PRODUCTION OF PHENOL

BACKGROUND OF THE INVENTION

1. Field of the Invention

This invention relates to the production of phenol and more particularly to a process for producing phenol and acetone from cumene hydroperoxide.

2. Description of the Prior Art

Phenol is an important organic chemical with a wide variety of industrial uses. It is used, for example, in the production of phenolic resins, bisphenol-A and caprolactam. A number of processes are currently in use for the production of phenol but the single process providing the largest proportion of the total production capacity is the cumene process which now accounts for over three quarters of the total U.S. production. The basic reaction involved in this process is the cleavage of cumene hydroperoxide into phenol and acetone:

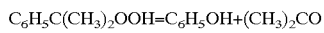

$$C_6H_5C(CH_3)_2OOH = C_6H_5OH + (CH_3)_2CO$$

On the industrial scale, the cumene hydroperoxide is usually treated with dilute sulphuric acid (5 to 25 percent concentration) at a temperature of about 50° to 70° C. After the cleavage is complete, the reaction mixture is separated and the oil layer distilled to obtain the phenol and acetone together with cumene, alpha-methylstyrene, acetophenone and tars. The cumene may be recycled for conversion to the hydroperoxide and subsequent cleavage. The phenol produced in this way is suitable for use in resins although further purification is required for a pharmaceutical grade product.

Although the process described above is capable of producing both phenol and acetone in good yields, it would be desirable to find a process which would reduce the need for the product separation and purification steps which are inherent in a homogeneous process and would avoid the need for environmentally hazardous liquid acids.

The heterogeneous cleavage of cumene hydroperoxide (CHP) over various solid acid catalysts has already been reported. For example, U.S. Pat. No. 4,490,565 discloses the use of zeolite beta in the cleavage of cumene hydroperoxide, whereas U.S. Pat. No. 4,490,566 discloses the use of a Constraint Index 1–12 zeolite, such as ZSM-5, in the same process.

U.S. Pat. No. 4,898,995 discloses a process for the coproduction of phenol and acetone by reacting cumene hydroperoxide over a heterogeneous catalyst consisting essentially of a heteropoly acid, such as 12-tungstophosphoric acid, on an inert support, such as silica, alumina, titania and zirconia. Such heteropoly acid catalysts are inherently unstable at temperatures in excess of 350° C.

None of the solid-acid catalysts currently proposed for cumene hydroperoxide cleavage exhibit the required combination of activity and selectivity to provide an acceptable replacement for sulfuric acid.

SUMMARY OF THE INVENTION

The present invention is directed to a process for producing phenol and acetone from cumene hydroperoxide, wherein the process comprises the step of contacting cumene hydroperoxide with a solid-acid catalyst comprising a sulfated transition metal oxide.

The process of the invention can achieve significant conversion of cumene hydroperoxide to phenol and acetone with low coproduction of impurities such as 4-cumylphenol, mesityl oxide and diacetone alcohol.

Preferably, the transition metal oxide includes at least one metal oxide selected from Groups IVB, IVA, VIIB and VIII of the Periodic Table.

Preferably, the transition metal oxide includes zirconia and more preferably includes zirconia together with an oxide of iron or oxides of iron and manganese.

Preferably, the sulfated transition metal oxide is calcined at a temperature of at least 400° C. and more preferably at least 500° C.

Preferably, said contacting step is conducted at a temperature of 20 to 150° C. and a pressure of atmospheric to 1000 psig and more preferably at a temperature of 40 to 120° C. and a pressure of atmospheric to 400 psig.

DESCRIPTION OF SPECIFIC EMBODIMENTS

It is known from, for example, the article by M. Hino et al in *Journal of the American Chemical Society,* Oct. 10, 1979, pages 6439–41, that solid acid catalysts useful for butane isomerization can be prepared by treating zirconia with sulfate ions and calcining the product. According to the invention, it has been found that a solid acid catalyst comprising a sulfated transition metal oxide, particularly a Group IVB metal oxide, such as zirconia, is an active and selective catalyst for the cleavage of cumene hydroperoxide.

The transition metal oxide used in the catalyst of the invention preferably includes at least one oxide of a Group IVB (Group 4 in the Group 1–18 classification system recommended by IUPAC) metal, such as titania or zirconia, a Group IVA (Group 14 in the Group 1–18 classification system recommended by IUPAC) metal, such as tin oxide, a Group VIIB (Group 7 in the Group 1–18 classification system recommended by IUPAC) metal, such as manganese oxide, and/or a Group VIII (Group 8 in the Group 1–18 classification system recommended by IUPAC) metal, such as iron oxide. Most preferably, the transition metal oxide includes zirconia. The catalyst of the invention may comprise more than one transition metal oxide, preferably a combination of zirconium and iron oxides or a combination of iron, manganese and zirconium oxides. The mixed transition metal oxide may be prepared by techniques known in the art, such as impregnation, coimpregnation, coprecipitation, physical admixture, etc.

The transition metal oxide is sulfated by treatment with a source of sulfate ion, such as sulfuric acid or, more preferably, ammonium sulfate. It is also possible to treat the transition metal oxide with a compound capable of forming sulfate ions on calcination, such as hydrogen sulfide, sulfur dioxide or mercaptans.

The catalyst used in the process of the invention preferably contains 0.5 to 20%, and more preferably 5 to 15%, of sulfate ion by weight of the catalyst.

After treatment with the source of sulfate ion, the transition metal oxide catalyst is calcined at a temperature of at least 400° C. and more preferably at least 500° C., typically from 500 to 800° C., for a period of 2 to 30 hours.

The cleavage reaction of the invention is effected by contacting the cumene hydroperoxide with the solid acid catalyst described above in the liquid phase at a temperature of 20 to 150° C., preferably 40 to 120° C., a pressure of atmospheric to 1000 psig, preferably atmospheric to 400 psig. To effect the contacting of the cumene hydroperoxide, the solid acid catalyst described above may be contained in a stationary or fluidized bed, and the contacting operation may take place continuously or batch-wise. If the contacting takes place continuously, the LHSV based on cumene hydroperoxide is within the range of 0.1 to 100 hr$^{-1}$, preferably 1 to 50 hr$^{-1}$. If the contacting takes place batch-wise, the residence time is within the range of 1 to 360 min, preferably 1 to 180 min. The cumene hydroperoxide is preferably dissolved in an organic solvent inert to the cleavage reaction, such as benzene, toluene, acetone and most preferably acetone. The use of a solvent is preferred so as assist in dissipating the heat of reaction (about 60 kcal/mol).

The invention will now be more particularly described with reference to the following Examples.

EXAMPLE 1

A 1 N solution of $(NH_4)_2SO_4$ was prepared by adding 3.3 g of ammonium sulfate to 50 g of deionized $H_2O$. Forty-two grams of the above solution was added slowly to 58 g of freshly prepared zirconium hydroxide and dried overnight at 85° C. A portion of this catalyst was calcined to 525° C. in flowing air for 3 hours.

EXAMPLE 2

To a 250-ml round bottom flask fitted with a condenser, stirrer and dropping funnel, and located in a water bath for temperature control, was charged a mixture of 100.0 g of acetone and 1.00 g of the catalyst of Example 1. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table 1 below shows the composition (mass %) of the reactant solution at 1.0 and 3.0 hours after the addition of the CHP was complete.

TABLE 1

|  | Feed | 1.0 hr | 3.0 hr |
| --- | --- | --- | --- |
| Acetone | 66.67 | 68.06 | 68.87 |
| Mesityl Oxide | 0.0 | 0.00 | 0.00 |
| Cumene | 2.56 | 2.56 | 2.57 |
| Phenol | 0.09 | 2.00 | 3.80 |
| α-Methyl Styrene | 0.07 | 0.15 | 0.19 |
| Acetophenone | 0.70 | 0.90 | 1.19 |
| 2-Phenyl-2-Propanol | 2.36 | 2.30 | 2.29 |
| Cumene Hydroperoxide | 26.93 | 23.59 | 20.54 |
| CHP Conversion |  | 12.4% | 23.8% |

EXAMPLE 3

Fifty grams of $ZrOCl_2 \cdot xH_2O$ and 0.8 g of $FeSO_4 \cdot 7H_2O$ were dissolved with stirring in 300 g of distilled water. The pH of the solution was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A solution of 0.7 g of $(NH_4)_2SO_4$ in 10 g of Dl water was prepared. Eight grams of this solution was added dropwise on to 12 g of the freshly prepared iron/zirconia prepared above. This material was dried overnight at 85° C. A portion of this catalyst was calcined to 525° C. in flowing air for 1 hour.

EXAMPLE 4

To a 250-ml round bottom flask fitted with a condenser, stirrer and dropping funnel, and located in a water bath for temperature control, was charged a mixture of 100.0 g of acetone and 1.00 g of the catalyst of Example 3. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table 2 below shows the composition (mass %) of the reactant solution at 1.0 and 3.0 hours after the addition of the CHP was complete.

TABLE 2

|  | Feed | 1.0 hr | 3.0 hr |
| --- | --- | --- | --- |
| Acetone | 66.67 | 74.75 | 77.08 |
| Mesityl Oxide | 0.0 | 0.00 | 0.00 |
| Cumene | 2.56 | 2.65 | 2.64 |
| Phenol | 0.09 | 12.41 | 15.72 |
| α-Methyl Styrene | 0.07 | 0.22 | 0.27 |
| Acetophenone | 0.70 | 1.76 | 1.19 |
| 2-Phenyl-2-Propanol | 2.36 | 2.01 | 1.71 |
| Cumene Hydroperoxide | 26.93 | 5.12 | 0.65 |
| CHP Conversion |  | 81.0% | 97.6% |

EXAMPLE 5

Thirty-eight grams of $TiOSO_4 \cdot xH_2SO_4 \cdot xH_2O$ were dissolved with stirring in 300 g of distilled water. The pH of the solution was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A solution of 0.7 g of $(NH_4)_2SO_4$ in 10 g of Dl water was prepared. 1.3 g of this solution were added dropwise on to 2 g of the freshly prepared titania prepared above. This material was dried overnight at 85° C. A portion of this catalyst was calcined to 525° C. in flowing air for 1 hour.

EXAMPLE 6

To a 250-ml round bottom flask fitted with a condenser, stirrer and dropping funnel, and located in a water bath for temperature control, was charged a mixture of 100.0 g of acetone and 1.00 g of the catalyst of Example 5. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table 3 below shows the composition (mass %) of the reactant solution at 1.0 and 3.0 hours after the addition of the CHP was complete.

TABLE 3

|  | Feed | 1.0 hr | 3.0 hr |
| --- | --- | --- | --- |
| Acetone | 66.67 | 70.00 | 74.02 |
| Mesityl Oxide | 0.0 | 0.00 | 0.00 |
| Cumene | 2.56 | 2.68 | 2.66 |
| Phenol | 0.09 | 4.25 | 10.02 |

TABLE 3-continued

|  | Feed | 1.0 hr | 3.0 hr |
|---|---|---|---|
| α-Methyl Styrene | 0.07 | 0.40 | 0.28 |
| Acetophenone | 0.70 | 3.64 | 2.71 |
| 2-Phenyl-2-Propanol | 2.36 | 2.33 | 1.93 |
| Cumene Hydroperoxide | 26.93 | 14.63 | 6.82 |
| CHP Conversion |  | 45.7% | 74.7% |

EXAMPLE 7

Twenty-five grams of $FeSO_4 \cdot 7H_2O$ were dissolved with stirring in 300 g of distilled water. The pH of the solution was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A solution of 0.7 g of $(NH_4)_2SO_4$ in 10 g of Dl water was prepared. 1.3 g of this solution were added dropwise on to 2 g of the freshly prepared iron oxide prepared above. This material was dried overnight at 85° C. A portion of this catalyst was calcined to 525° C. in flowing air for 1 hour.

EXAMPLE 8

To a 250-ml round bottom flask fitted with a condenser, stirrer and dropping funnel, and located in a water bath for temperature control, was charged a mixture of 90.0 g of acetone and 1.00 g of the catalyst of Example 7. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table 4 below shows the composition (mass %) of the reactant solution at 1.16 and 2.67 hours after the addition of the CHP was complete.

TABLE 4

|  | Feed | 1.0 hr | 3.0 hr |
|---|---|---|---|
| Acetone | 64.29 | 64.57 | 66.33 |
| Mesityl Oxide | 0.0 | 0.00 | 0.00 |
| Cumene | 2.75 | 2.81 | 2.88 |
| Phenol | 0.10 | 1.36 | 3.40 |
| α-Methyl Styrene | 0.08 | 0.29 | 0.44 |
| Acetophenone | 0.74 | 2.24 | 4.01 |
| 2-Phenyl-2-Propanol | 2.46 | 2.64 | 2.70 |
| Cumene Hydroperoxide | 28.89 | 24.78 | 18.01 |
| CHP Conversion |  | 14.1% | 37.6% |

EXAMPLE 9

Five hundred grams of $ZrO(Cl)_2 \cdot xH_2O$ were dissolved with stirring in 3.0 liters of distilled water. Another solution containing 260 g of conc. $NH_4OH$ and 3.0 liters of distill water was prepared. Both solutions were heated to 60° C. These two heated solutions were combined at the rate of 50 ml/min using a nozzle mixing. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C.

EXAMPLE 10

A solution of 0.7 g of $(NH_4)_2SO_4$ in 10 g of Dl water was prepared. Eight grams of this solution was first combined with 0.5 g of $FeSO_4 \cdot 7H_2O$ and 0.3 g of $MnSO_4 \cdot H_2O$. This solution was added dropwise on to 12 g of the freshly prepared zirconia prepared in Example 9. This material was dried overnight at 85° C. A portion of this catalyst was calcined to 525° C. in flowing air for 1 hour.

EXAMPLE 11

To a 250-ml round bottom flask fitted with a condenser, stirrer and dropping funnel, and located in a water bath for temperature control, was charged a mixture of 100.0 g of acetone and 1.00 g of the catalyst of Example 10. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table 5 below shows the composition (mass %) of the reactant solution at 1.0 and 3.0 hours after the addition of the CHP was complete.

TABLE 5

|  | Feed | 1.0 hr | 3.0 hr |
|---|---|---|---|
| Acetone | 66.67 | 72.16 | 75.02 |
| Mesityl Oxide | 0.0 | 0.00 | 0.00 |
| Cumene | 2.56 | 2.61 | 2.63 |
| Phenol | 0.09 | 8.02 | 12.52 |
| α-Methyl Styrene | 0.07 | 0.21 | 0.22 |
| Acetophenone | 0.70 | 1.86 | 1.83 |
| 2-Phenyl-2-Propanol | 2.36 | 2.20 | 2.00 |
| Cumene Hydroperoxide | 26.93 | 11.86 | 4.64 |
| CHP Conversion |  | 56.0% | 74.6% |

EXAMPLE 12

A solution of 0.7 g of $(NH_4)_2SO_4$ in 10 g of Dl water was prepared. Eight grams of this solution was first combined with 0.5 g of $FeSO_4 \cdot 7H_2O$ and then this solution was added dropwise on to 12 g of the freshly prepared zirconia prepared in Example 9. This material was dried overnight at 85° C. A portion of this catalyst was calcined to 525° C. in flowing air for 1 hour.

EXAMPLE 13

To a 250-ml round bottom flask fitted with a condenser, stirrer and dropping funnel, and located in a water bath for temperature control, was charged a mixture of 100.0 g of acetone and 1.00 g of the catalyst of Example 12. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table 6 below shows the composition (mass %) of the reactant solution at 1.0 and 3.0 hours after the addition of the CHP was complete.

TABLE 6

|  | Feed | 1.0 hr | 3.0 hr |
| --- | --- | --- | --- |
| Acetone | 66.67 | 71.69 | 73.78 |
| Mesityl Oxide | 0.0 | 0.00 | 0.00 |
| Cumene | 2.56 | 2.59 | 2.61 |
| Phenol | 0.09 | 7.61 | 11.00 |
| α-Methyl Styrene | 0.07 | 0.19 | 0.21 |
| Acetophenone | 0.70 | 1.41 | 1.63 |
| 2-Phenyl-2-Propanol | 2.36 | 2.17 | 2.08 |
| Cumene Hydroperoxide | 26.93 | 13.49 | 7.67 |
| CHP Conversion |  | 56.0% | 71.5% |

What we claim is:

1. A process for producing phenol and acetone from cumene hydroperoxide, wherein said process comprises the step of contacting cumene hydroperoxide with a solid-acid catalyst comprising a sulfated transition metal oxide.

2. The process of claim 1, wherein the transition metal oxide is selected from oxides of Group IVB, Group IVA, Group VIIB and Group VIII the Periodic Table and mixtures thereof.

3. The process of claim 1, wherein the transition metal oxide is selected from titania, zirconia, tin oxide, manganese oxide and iron oxide and mixtures thereof.

4. The process of claim 1, wherein the transition metal oxide includes zirconia.

5. The process of claim 1, wherein the transition metal oxide includes a combination of zirconium and iron oxides or a combination of iron, manganese and zirconium oxides.

6. The process of claim 1, wherein the sulfated transition metal oxide is calcined at a temperature of at least 400° C.

7. The process of claim 1, wherein the sulfated transition metal oxide is calcined at a temperature of at least 500° C.

8. The process of claim 1, wherein said contacting step is conducted at a temperature of 20 to 150° C. and a pressure of atmospheric to 1000 psig.

9. The process of claim 1, wherein said contacting step is conducted at a temperature of 40 to 120° C. and a pressure of atmospheric to 400 psig.

* * * * *